US00PP33778P2

(12) United States Plant Patent
Korlipara

(10) Patent No.: US PP33,778 P2
(45) Date of Patent: Dec. 21, 2021

(54) ***ECHINACEA* PLANT NAMED 'TNECHPS'**

(50) Latin Name: ***Echinacea* spp.**
Varietal Denomination: TNECHPS

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 17/165,073

(22) Filed: Feb. 2, 2021

(51) Int. Cl.
*A01H 5/02* (2018.01)
*A01H 6/14* (2018.01)

(52) U.S. Cl.
USPC ..... Plt./428
CPC ..... *A01H 6/14* (2018.05)

(58) Field of Classification Search
USPC ..... Plt./428
CPC ..... A01H 5/02
See application file for complete search history.

(56) References Cited

PUBLICATIONS https://www.perishablenews.com/floral/terra-nova-nurseries-introduces-sneak-peek-of-echinacea-prima-saffron/; Apr. 2, 2020; 1 page.*

* cited by examiner

*Primary Examiner* — Kent L Bell
(74) *Attorney, Agent, or Firm* — Klarquist Sparkman, LLP

(57) ABSTRACT

A new and distinct *Echinacea* plant named 'TNECHPS' characterized by medium orange to soft gold multicolored ray florets, an amazing number of inflorescences starting in the first season, a very compact habit, very long bloom time with excellent rebloom, ray florets held horizontally, and excellent vigor.

1 Drawing Sheet

Botanical denomination: *Echinacea* spp.
Variety designation: 'TNECHPS'.
Trademark designation: Prima Saffron™.

BACKGROUND OF THE INVENTION

The present invention relates to a new and distinct cultivar of *Echinacea* and given the cultivar name 'TNECHPS'. *Echinacea* is in the family Asteraceae. The new cultivar is part of a planned breeding program for a landscape series with very compact habits and profuse inflorescences. The exact parents of this selection are unknown, unnamed, proprietary interspecific hybrids bred from *Echinacea paradoxa, Echinacea purpurea*, and *Echinacea tennesseensis.*

Compared to *Echinacea* 'Leilani' (U.S. Plant Pat. No. 23,526), the new cultivar is much shorter and the inflorescences are smaller.

This new *Echinacea* cultivar is uniquely distinguished by:

1. medium orange to soft gold multicolored ray florets,
2. an amazing number of inflorescences starting in the first season,
3. a very compact habit,
4. very long bloom time with excellent rebloom,
5. ray florets held horizontally, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding asexual propagations. The present invention has not been evaluated under all possible environmental conditions. The phenotype may vary with variations in environment without a change in the genotype of the plant.

BRIEF DESCRIPTION OF THE DRAWING

FIG. 1 shows 8-month-old *Echinacea* 'TNECHPS' plants growing in the trial field in full sun in early August in Canby, Oreg.

DETAILED PLANT DESCRIPTION

The following is a detailed description of the new *Echinacea* cultivar based on observations of 9-month-old specimens growing in the trial field in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on *The Royal Horticultural Society Colour Chart,* $5^{th}$ edition, 2007.

Plant:

*Type*.—Herbaceous perennial.
*Hardiness*.—USDA Zones 4 to 9.
*Size*.—Grows to 24 cm wide and 31 cm tall to top of inflorescences.
*Form*.—Basal clump, with 4 to 6 stems from the base.
*Vigor*.—Excellent.
*Roots*.—Fibrous, with many downward growing and few laterals, ivory in color, Yellow White between 158C and 158D, roots develop easily from cuttings from the crown.

Leaf (stem):

*Type*.—Simple.

*Shape*.—Lanceolate.

*Arrangement*.—Alternate.

*Blade size*.—Grows to 22 cm long (usually 12 cm to 14 cm long) and 3.2 cm wide.

*Margins*.—Entire.

*Apex*.—Acuminate.

*Base*.—Attenuate.

*Surface texture*.—Strigose on both sides.

*Venation*.—Pinnate, Yellow Green 144D on both sides.

*Color*.—Topside Green N137D, bottom side closest to Yellow Green 146A.

*Petiole description*.—Clasping, grows to 7 cm long and 3 mm wide, scabrous, narrow leafy edges which fold upwards, Yellow Green 146C.

Inflorescence:

*Type*.—Composite on terminal stalked heads.

*Flowering stem*.—Grows to 31 cm tall from the base of the plant to the terminal inflorescence and can grow to 10 cm long from the top stem leaf to the base of an inflorescence; unbranched to branched, with 1 to 8 inflorescences per stem; diameter growing to 7 mm wide near the inflorescence; strigose; Yellow Green 145C stippled 147B, with shadows of Greyed Purple 186C when grown exposed to high light.

*Size*.—Grows to 10 cm wide and 6.5 cm deep as disc enlarges.

*Form*.—Ray florets held horizontally, curving down in old inflorescences, mature disc is conic.

*Immature inflorescence* (*bud*).—4 cm wide and 2 cm deep, ray florets held upright at 35 degree angle and rolled up so only the back color shows, Greyed Red 184A except tip Yellow Green 145C, disc color Green 137B with bracts Greyed Purple 187D.

*Ray florets*.—Without pistil or stamen, 15 to 22 in number, grow to 42 mm long and 12 mm wide, oblanceolate with the tip two-to-three-toothed (each acute), entire margins, base attenuate, glabrous on both sides; fully open florets topside Orange 23A and 23B blending to base Orange N25A, bottom side Orange N25D with streaks of Red Purple 59C; florets fade gradually to top side Orange 26C, bottom side Yellow-Orange 22C with Red Purple 59C at base.

*Disc*.—Flat becoming conic, becoming 37 mm deep and 39 mm wide with maturity, Greyed Purple N186A in background with bracts Orange N25C with tips Greyed Purple 187A.

*Disc florets*.—About 400 in number, each with 1 pistil and 4 stamen, grow to 10 mm long and 2 mm wide, each with one persistent, very stiff linear bract (15 mm long with the top 1 mm Greyed Purple 187B blending to 4 mm Orange 25C to 5 mm Green 147B); corolla 5 mm long and 2 mm wide, tubular, 5 lobed, glabrous, Yellow Green 139C on lobes blending to 145C; pistil 10 mm long, ovary 3 mm long, White 155D with top between Yellow Green 143B and 143C, style 5 mm long White NN155A, 2-branched stigma spreading 3 mm wide, Greyed Purple 187B; stamen 5 mm long, filaments 2 mm long and between White NN155A and NN155B, anthers 3 mm long and Greyed Purple N187A, pollen, plentiful, Yellow 13B.

*Involucral bracts*.—In 4 leafy series, area grows to 37 mm wide and 11 mm deep, lobes lanceolate in shape, reflexed, grow to 11 mm long and 5 mm wide, Green N137B, margins strigose, tip acute, strigose on both sides.

*Receptacle*.—Grows to 15 mm wide and 23 mm deep, White NN155A.

*Bloom period*.—June through October in Canby, Oreg.

*Fragrance*.—Moderate, sweet.

*Lastingness*.—Each inflorescence lasts about 3 weeks in Canby, Oreg.

Seeds: 3 mm long and 2.5 mm wide, oval, Brown N200A.

*Fertility*.—Moderate.

Disease and pests: No pests or diseases have been observed on plants grown under commercial conditions in Canby, Oreg. No resistances are known.

I claim:

1. A new and distinct *Echinacea* plant as herein illustrated and described.

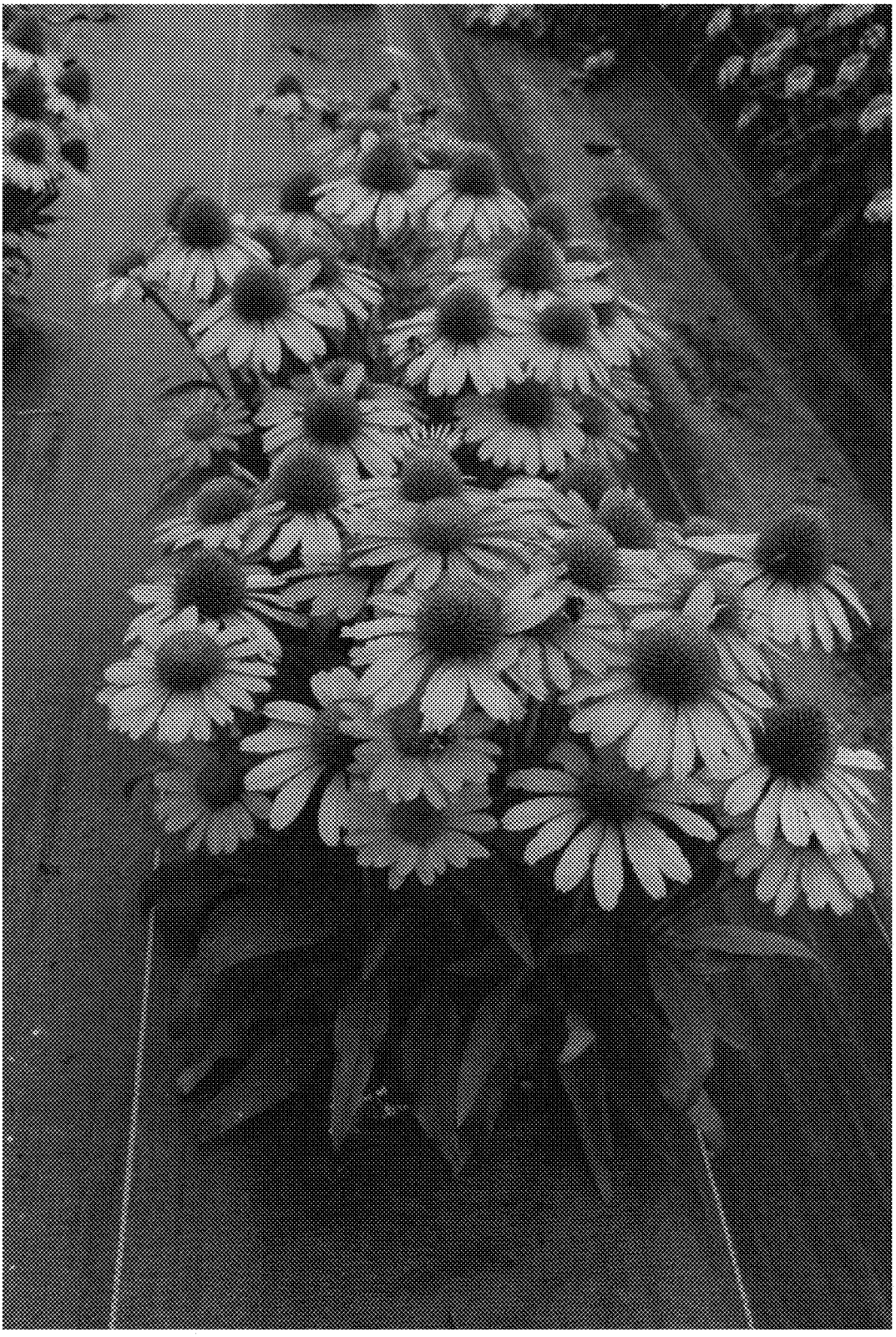

* * * * *